(12) United States Patent
Petruzzelli et al.

(10) Patent No.: US 9,326,690 B2
(45) Date of Patent: May 3, 2016

(54) PATIENT MONITOR WITH VISUAL RELIABILITY INDICATOR

(75) Inventors: Joe Petruzzelli, Paramus, NJ (US); Cadathur Rajagopalan, Dumont, NJ (US)

(73) Assignee: SHENZHEN MINDRAY BIO-MEDICAL ELECTRONICS CO. LTD., Shenzhen (CN)

( * ) Notice: Subject to any disclaimer, the term of this patent is extended or adjusted under 35 U.S.C. 154(b) by 1116 days.

(21) Appl. No.: 12/251,408

(22) Filed: Oct. 14, 2008

(65) Prior Publication Data

US 2010/0094096 A1    Apr. 15, 2010

(51) Int. Cl.
| | |
|---|---|
| G06F 19/00 | (2011.01) |
| A61B 5/00 | (2006.01) |
| A61B 5/0205 | (2006.01) |
| G06F 3/0481 | (2013.01) |

(52) U.S. Cl.
CPC ............ *A61B 5/0205* (2013.01); *A61B 5/7221* (2013.01); *A61B 5/743* (2013.01); *G06F 3/0481* (2013.01); *G06F 19/3431* (2013.01); *A61B 2560/0276* (2013.01)

(58) Field of Classification Search
USPC .................... 600/300, 301; 128/903–905, 920
See application file for complete search history.

(56) References Cited

U.S. PATENT DOCUMENTS

| | | | |
|---|---|---|---|
| 5,912,656 A * | 6/1999 | Tham et al. .................... 345/418 |
| 6,097,390 A * | 8/2000 | Marks ........................... 715/772 |
| 6,337,699 B1 * | 1/2002 | Nielsen ......................... 715/837 |
| 6,414,697 B1 * | 7/2002 | Amro et al. .................... 715/772 |
| 6,658,276 B2 * | 12/2003 | Kianl et al. .................... 600/322 |
| 6,675,031 B1 | 1/2004 | Porges et al. |
| 6,934,916 B1 * | 8/2005 | Webb et al. .................... 715/772 |
| 8,166,412 B2 * | 4/2012 | Jain et al. ...................... 715/772 |
| 2002/0035315 A1 * | 3/2002 | Ali et al. ........................ 600/300 |
| 2004/0014013 A1 * | 1/2004 | Diesel et al. ................... 434/118 |
| 2004/0122666 A1 * | 6/2004 | Ahlenius ....................... 704/231 |
| 2005/0128065 A1 * | 6/2005 | Kolpasky et al. ............. 340/461 |
| 2006/0167362 A1 * | 7/2006 | Neumann et al. ............. 600/504 |
| 2006/0211925 A1 * | 9/2006 | Lamego et al. ............... 600/310 |
| 2006/0238358 A1 * | 10/2006 | Al-Ali et al. ................ 340/573.1 |
| 2008/0103375 A1 * | 5/2008 | Kiani ............................ 600/323 |
| 2009/0106684 A1 * | 4/2009 | Chakra et al. ................. 715/772 |
| 2009/0164933 A1 * | 6/2009 | Pederson et al. .............. 715/772 |
| 2009/0187563 A1 * | 7/2009 | Chen ................................ 707/5 |

(Continued)

OTHER PUBLICATIONS

Datex-Ohmeda, "Perfusion Index," Dec. 14, 2005, http://www.gehealthcare.com/usen/oximetry/docs/OS4211.pdf.*

(Continued)

*Primary Examiner* — Gary Jackson
*Assistant Examiner* — Davin Sands
(74) *Attorney, Agent, or Firm* — Kory D. Christensen; Stoel Rives LLP

(57) ABSTRACT

A patient monitor configured to display patient information in a display area. The patient information is indicative of at least one physiological parameter of a patient and includes at least one unitary display element in the display area that indicates simultaneously both a quantitative value and a reliability indication of the physiological parameter. An appearance of the display element transitions so as to represent a plurality of different reliability levels, including at least a first reliability level, a second reliability level, and at least one intermediary reliability level between the first and second reliability levels.

15 Claims, 12 Drawing Sheets

(56) References Cited

U.S. PATENT DOCUMENTS

2009/0192745 A1* 7/2009 Kamath et al. .................. 702/85
2010/0145170 A1* 6/2010 Ayers et al. .................. 600/324

OTHER PUBLICATIONS

Aspect Medical Systems, A-2000 Bispectral Index (BIS) Monitoring System Operating Manual, 2006.

* cited by examiner

PATIENT MONITOR WITH VISUAL RELIABILITY INDICATOR

BACKGROUND OF THE INVENTION (1) Field of the Invention

The present invention generally relates to patient monitors.

(2) Description of Related Art

Patient monitors are used to monitor numerous physiologic parameters. Some of these parameters, like non-invasive blood pressure, cardiac output, cardiac index, etc., are typically measured at predetermined time intervals and are displayed on the patient monitor until a new reading is taken. In the interim between readings, however, the displayed physiologic readings may no longer be consistent with the monitored patient's actual condition. Further, the initial reading itself may be unreliable because of problems associated with the measurement of the physiologic parameter. Errors could be introduced, for example, by a misplaced sensor or external noise or artifact pickup. Moreover, the reliability of the displayed values of some measured parameters depends on such factors as whether the measurement algorithms has converged, or has a high enough level of statistical confidence, etc.

Given the need to provide expedient care and the obvious serious consequences of basing medical treatment related decisions on stale or otherwise less reliable patient data, there is a need on the part of clinicians to quickly comprehend how reliable, e.g., current, or valid, or accurate, the displayed physiologic readings are.

Some patient monitors on the market, for example, Datascope Patient Monitoring's Spectrum and Passport 2, indicate the elapsed time since a physiologic parameter was measured using a counter adjacent to the reading, i.e., separate from and not unitary with the reading. Others, such as certain Aspect Medical monitors, communicate the quality of a patient signal using a bar graph adjacent to the reading (also separate from and not unitary with the reading). Further, the monitor disclosed in U.S. Pat. No. 6,675,031 displays assessments of quality, such as "INVALID MEASUREMENT" or "WEAK SIGNAL," next to the displayed patient parameter. These display elements, such as counters, bar graphs, and textual assessments however, do not always stand out, and are easily overlooked in a busy hospital setting. Further, given the large amount of information displayed on a typical patient monitor, the counter or bar graph may not always be read in the context of the physiologic parameter it is actually associated with. They also require the viewer to see, mentally associate, and interpret two different on-screen display elements, usually in a rushed, cluttered and distracting environment.

Certain patient monitors replace displayed patient parameters with dashed lines to the extent the reading exceeds a predetermined threshold error level. One or more Aspect Medical monitors replace the patient parameter numeral with an outline of the numeral or remove the numeral altogether when such a threshold is exceeded, indicating the numerical data may be unreliable.

BRIEF SUMMARY OF THE INVENTION

A patient monitor according to an exemplary embodiment of the present invention is adapted to graphically convey how reliable, e.g., current, or valid, or accurate, a measured physiologic parameter is.

In an exemplary embodiment, the patient monitor includes a screen adapted to display at least one unitary display element, e.g., an alphanumeric character, and/or a processor. The processor may be adapted to keep track of the elapsed time since the last patient measurement and to modify the display element in a manner representative of such elapsed time. The patient monitor may also be in communication with a sensor adapted to measure the physiologic parameter or an internal or external memory unit with pre-stored data, e.g., pre-stored patient data.

In an exemplary embodiment, the fill used to display the physiologic parameter is removed over predetermined intervals, which may be regular or irregular. When the physiologic parameter is first measured, an alphanumeric character, e.g., a numeral quantifying it, is displayed in outline format with the number shown fully filled in. After a predetermined amount of time, past which the reading is considered not to be current, e.g., 20 to 30 minutes for non-invasive blood pressure readings and four to six hours for cardiac output or cardiac index readings, only an outline of the displayed number is shown. At intermediary times, the number is shown partially filled to different levels. Alternatively, the numeral may start empty and be displayed in outline format and over time be populated with more and more fill.

In an exemplary embodiment, the color or type of fill can also be used to communicate the validity or accuracy of the physiological parameter reading. In one embodiment, thick cross hatching is used to communicate a high confidence level in the reading and thinner cross hatching is used to communicate a lower level of confidence in the reading.

A patient monitor according to an exemplary embodiment is configured to display patient information in a display area. The patient information is indicative of at least one physiological parameter of a patient and includes at least one unitary display element in the display area. The display element indicates simultaneously both a quantitative value and a qualitative, for example, reliability, indication of the physiological parameter. An appearance of the display element transitions so as to represent a plurality of different reliability levels, including at least a first reliability level, a second reliability level, and at least one intermediary reliability level between the first and second reliability levels.

In an exemplary embodiment, an appearance of the display element is modified over time in a manner representative of an elapsed time since the physiologic parameter was measured.

In an exemplary embodiment, an appearance of the display element is representative of a degree of accuracy or validity of the physiologic parameter as measured.

In an exemplary embodiment, the display element is circumscribed by an outline. The appearance of the display element is modified over time by changing a fill populating the outline.

In an exemplary embodiment, a predetermined amount of fill is removed or added, e.g., on regular or irregular predetermined intervals.

In an exemplary embodiment, an appearance of the display element is modified over time by changing a color of at least a portion of the display element.

In an exemplary embodiment, the monitor includes a screen adapted to display the display element.

In an exemplary embodiment, the monitor includes a processor adapted to keep track of the elapsed time and to modify the display element in a manner representative of such elapsed time. The processor used to run the monitor can be adapted to handle these functions. Therefore, additional hardware is not necessary.

In an exemplary embodiment, the monitor includes a sensor adapted to measure the physiologic parameter.

A method for patient monitoring according to an exemplary embodiment of the present invention comprises the steps of: (i) displaying a unitary display element representative of a physiologic parameter and indicating simultaneously both a quantitative value and a reliability indication of the physiological parameter; and (ii) accordingly modifying an appearance of the display element. The appearance of the display element transitions so as to represent a plurality of different reliability levels, including at least a first reliability level, a second reliability level, and at least one intermediary reliability level between the first and second reliability levels.

In an exemplary embodiment, the appearance of the display element is modified over time by changing a color of at least a portion of the display element.

A patient monitor according to an exemplary embodiment is configured to display patient information in a display area. The patient information is indicative of at least one physiological parameter of a patient and includes at least one unitary display element in the display area that indicates simultaneously both a quantitative value and a reliability indication of the physiological parameter. An appearance of the display element is modified over time in a manner representative of an elapsed time since the physiologic parameter was measured.

A method for patient monitoring according to an exemplary embodiment includes the steps of: (i) displaying a unitary display element representative of a physiologic parameter, the display element simultaneously indicating both a quantitative value and a reliability of the physiological parameter; and (ii) accordingly modifying an appearance of the display element over time. The modification is representative of an elapsed time since the physiologic parameter was measured.

Using the patient monitor with the novel features described, a clinician no longer needs to (i) remember that a particular reading may not be current or accurate, (ii) realize that there might be a reliability indicator on another portion of the screen (most monitors do not include such an indicator), and (iii) then seek out the reliability indicator. The manner in which the patient parameters of the present invention are graphically depicted, i.e., using a unitary display element which simultaneously communicates a quantitative value and a reliability indication of the physiological parameter, naturally reminds the clinician, when appropriate, that reliability may be an issue and clearly communicates the reliability of the information.

Reference throughout this specification to "an embodiment" or "an exemplary embodiment" means that a particular feature, structure, or characteristic described in connection with the embodiment is included in at least one embodiment of the present invention. Thus, the appearances of these phrases in various places throughout this specification are not necessarily all referring to the same embodiment. Furthermore, the particular features, structures, or characteristics may be combined in any suitable manner in one or more embodiments.

An example embodiment of the present invention is described in more detail below with reference to the appended Figures. The foregoing description and examples have been set forth as mere illustrations and are not intended to be limiting. Each of the disclosed aspects and embodiments may be considered individually or in combination with other aspects, embodiments, and variations thereof. The steps of the methods described herein are not confined to any particular order of performance.

DETAILED DESCRIPTION OF THE INVENTION

Figure 1:
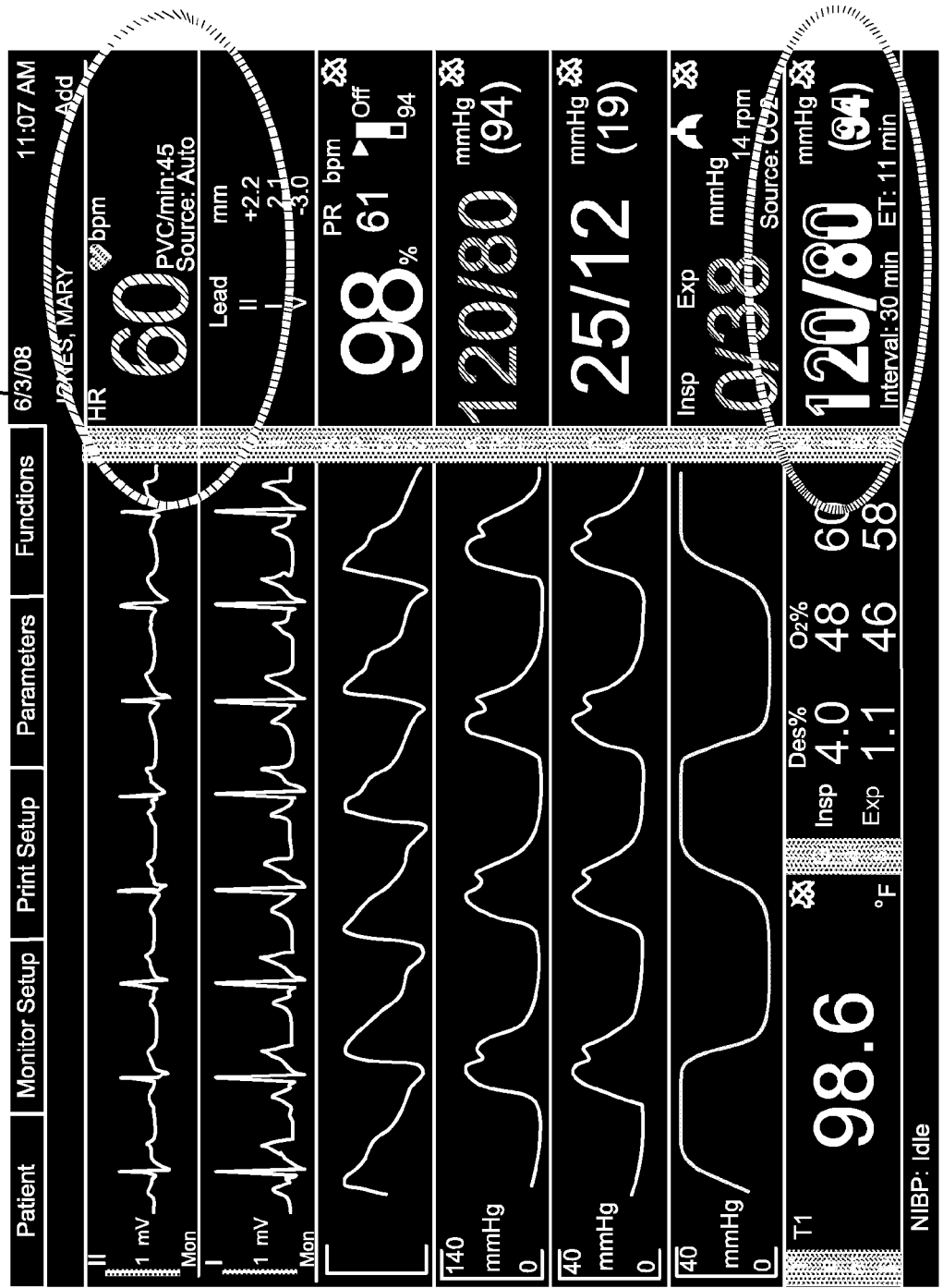
FIG. 1 is an illustration of a patient monitor screen according to an exemplary embodiment of the present invention.

FIG. 1 is a view of a patient monitor 10 according to one exemplary embodiment of the present invention. As can be seen in the exemplary screen shot illustrated in FIG. 1, a typical patient monitor will usually display various patient parameters and waveforms such as heart rate (HR), an electrocardiograph waveform (ECG), ST segment deviation measurements (ST), a plethysmographic signal and the oxygen saturation ($SpO_2$), an arterial blood pressure waveform (ART), a pulmonary artery pressure waveform (PA), a carbon dioxide waveform ($CO_2$), and non-invasive blood pressure (NIBP). The displayed parameters are generally based on physiologic signals acquired from patients using suitable invasive or non-invasive sensors, such as electrodes, or a pulse-oximetry sensor, etc., and communicated to the patient monitor through a cable or wirelessly. The displayed parameters may also be based on stored data, e.g., stored patient data.

Figure 2:
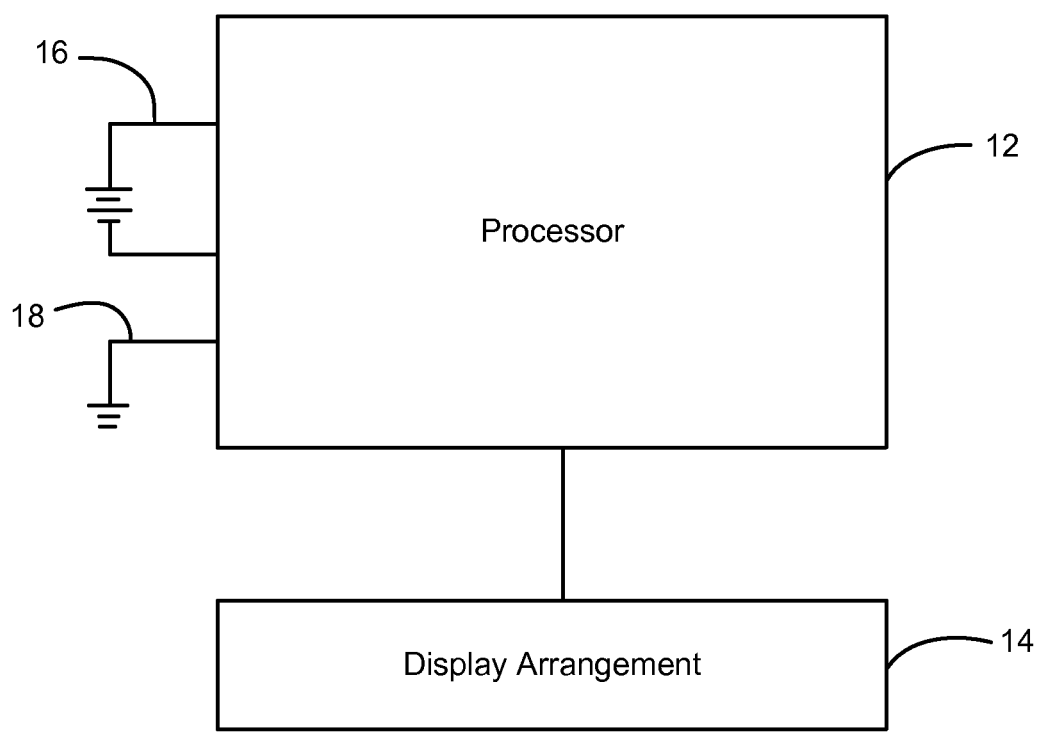
FIG. 2 is a block diagram of a patient monitor according to an exemplary embodiment of the present invention.

FIG. 2 is a block diagram of the patient monitor 10. A processor 12 communicates with a display arrangement 14, a power source 16, and a ground 18. The display arrangement 14 may be the display itself and may be of any known type, such as a phosphorescent screen, LCD, or OLED, etc.

The processor 12 contains processing circuitry for evaluating and implementing measurement algorithms to acquire patient signals and process these to derive values of patient parameters and to display them on the patient monitor 10.

Depending on the parameter(s) of interest, the processor 12 may optionally also keep track of the interval time between measurements for displayed physiologic parameters that are measured periodically, such as NIBP. The processor 12 displays these parameters via the display arrangement 14. If desired, other information such as elapsed time may be displayed, e.g., below such physiologic parameters, and may be used to control the display of the physiologic parameter consistent with the graphical representations detailed below.

As can be seen in the encircled lower right hand section of the patient monitor 10 in FIG. 1, the fill color at the top portion of the numeral quantifying the NIBP parameter is partially emptied. FIGS. 3A-3E represent enlargements of this portion of the monitor 10 at different points in time. As can be seen in these figures, the representation of the NIBP readings in mmHg, i.e., 120/80 (94), changes over time to reflect the reliability of these displayed parameters, which in this case takes into account the elapsed time since the readings were taken. The numerical values themselves do not change (only their graphical representations change) because new readings have not been taken from the patient. The interval between readings in this example is 30 minutes. Thus, in this embodiment, the qualitative indication of the parameter is not necessarily a function of the quantitative indication, even though the same display element may be used to convey both.

Figure 3A:
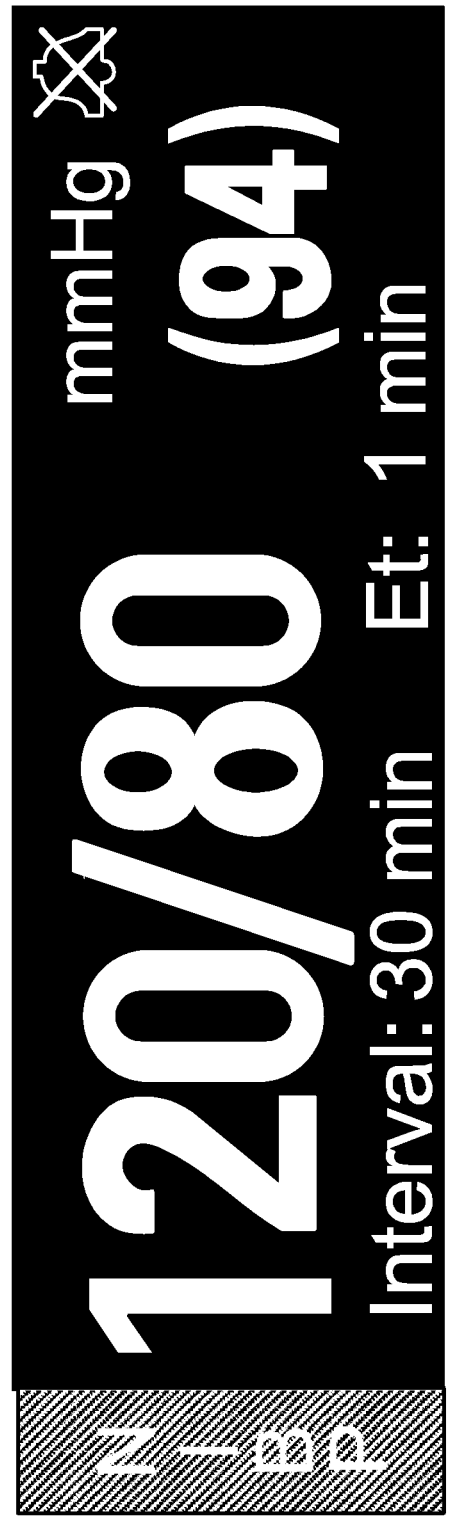
FIG. 3A is an illustration of the encircled lower right hand corner section of the patient monitor of FIG. 1 one minute after the patient's non invasive blood pressure (NIBP) was measured.

FIG. 3A represents a point in time one minute after the NIBP reading was taken from the patient. The NIBP readings (120/80 (94)) are completely solid, which indicates that the readings are still considered current, i.e., representative of the patient's actual condition. FIGS. 3B, 3C, 3D, and 3E illustrate NIBP measurements 11, 17, 24, and 29 minutes, respectively, after the readings were taken. NIBP measurements (120/80 (94) mmHg) in FIG. 3E are completely hollowed out and shown in outline format to indicate that the readings are old and no longer representative of the patient's current state. The more "hollow" the displayed number, the less reliable it is considered to be, in this example due to the elapsed time since the measurement was made.

Modification of the NIBP representation, e.g., removal of fill from the NIBP readings, can be done at regular or irregular intervals. Certain readings may be considered to be current for longer periods than others, in which case the readings can retain their original solid fill appearance for extended periods of time. The processor 12 may be programmed to modify the appearance of different displayed parameters differently based on the above-discussed properties.

Figure 3B:
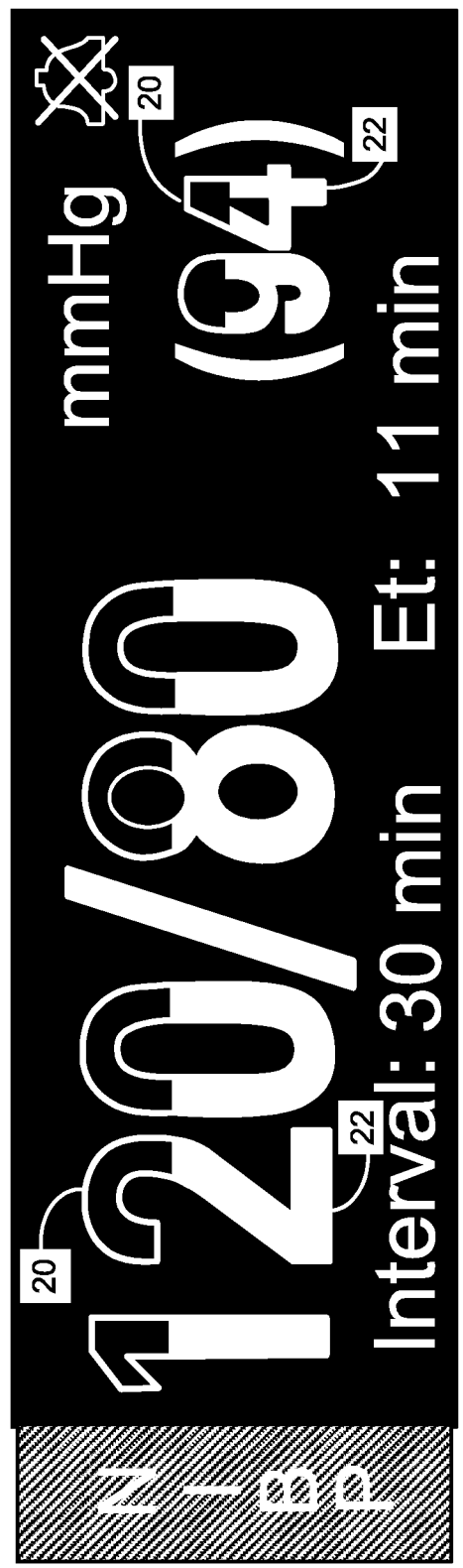
FIG. 3B is a view of the encircled lower right hand corner section of the patient monitor of FIG. 1 eleven minutes after the NIBP readings were taken.
Figure 3C:
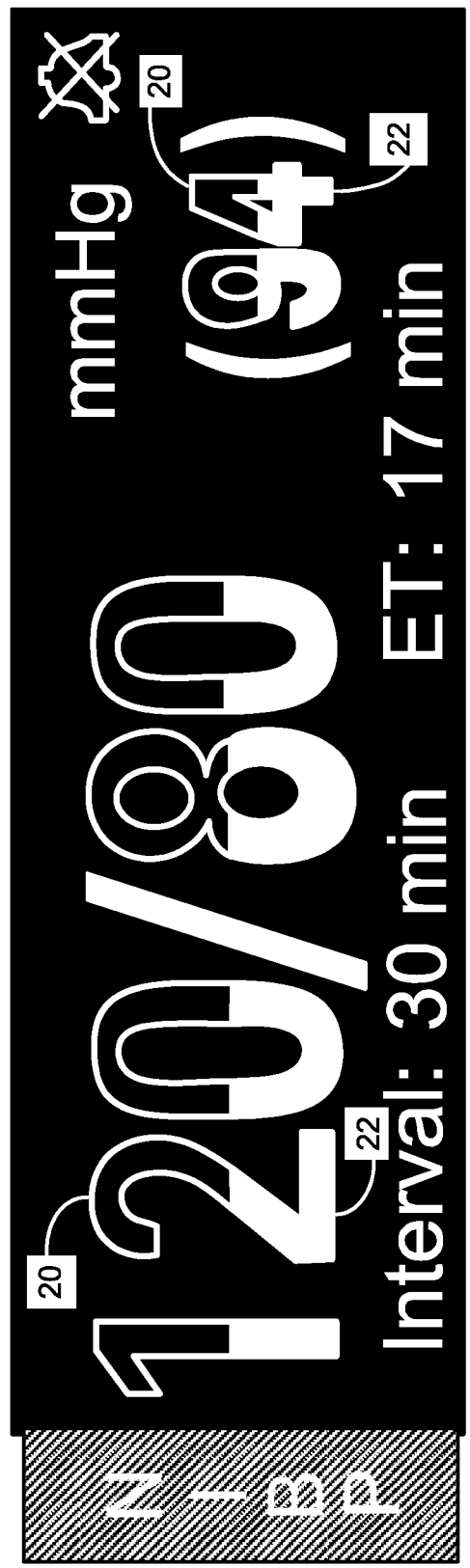
FIG. 3C is a view of the encircled lower right hand corner section of the patient monitor of FIG. 1 seventeen minutes after the NIBP readings were taken.
Figure 3D:
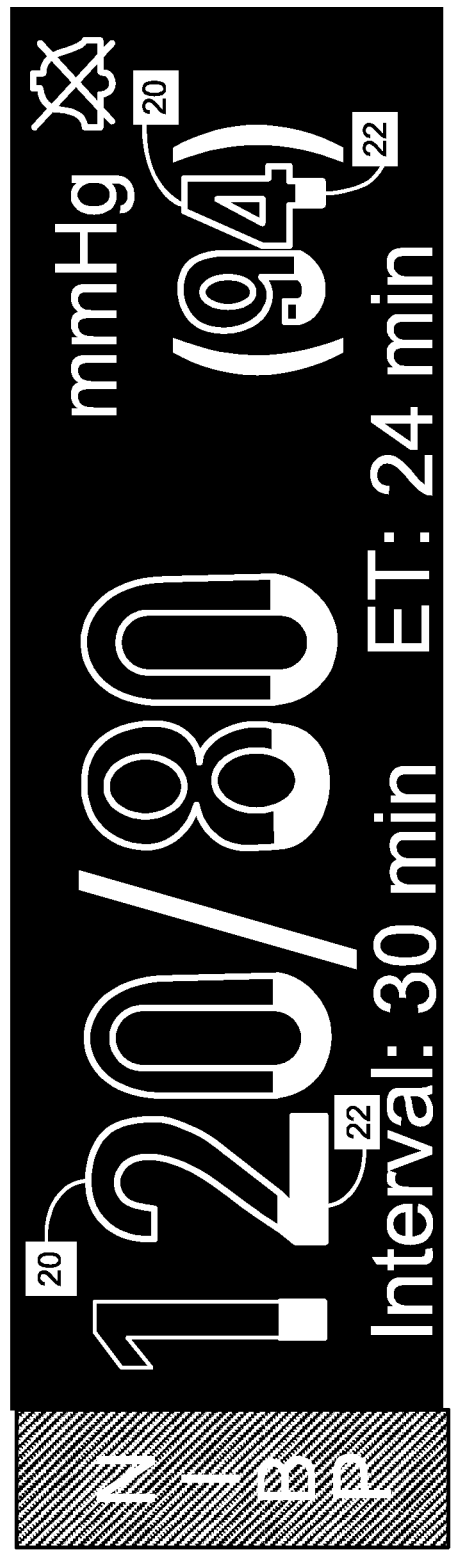
FIG. 3D is an illustration of the encircled lower right hand corner section of the patient monitor of FIG. 1 twenty four minutes after the NIBP readings were taken.
Figure 3E:
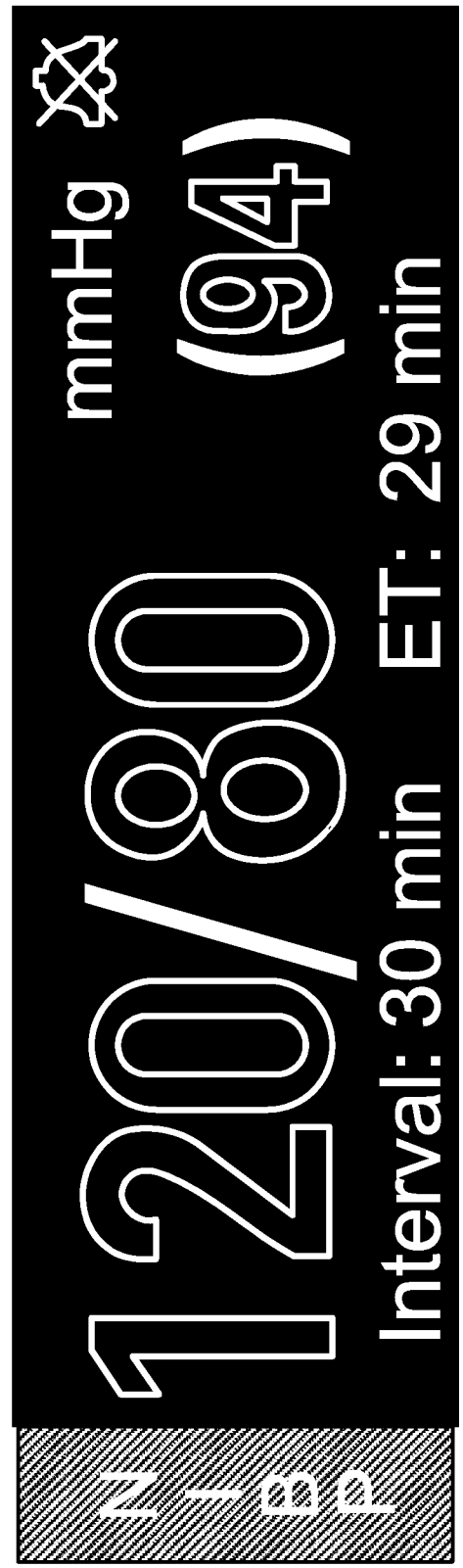
FIG. 3E is an illustration of the encircled lower right hand corner section of the patient monitor of FIG. 1 twenty nine minutes after the NIBP readings were taken.
Figure 4A:
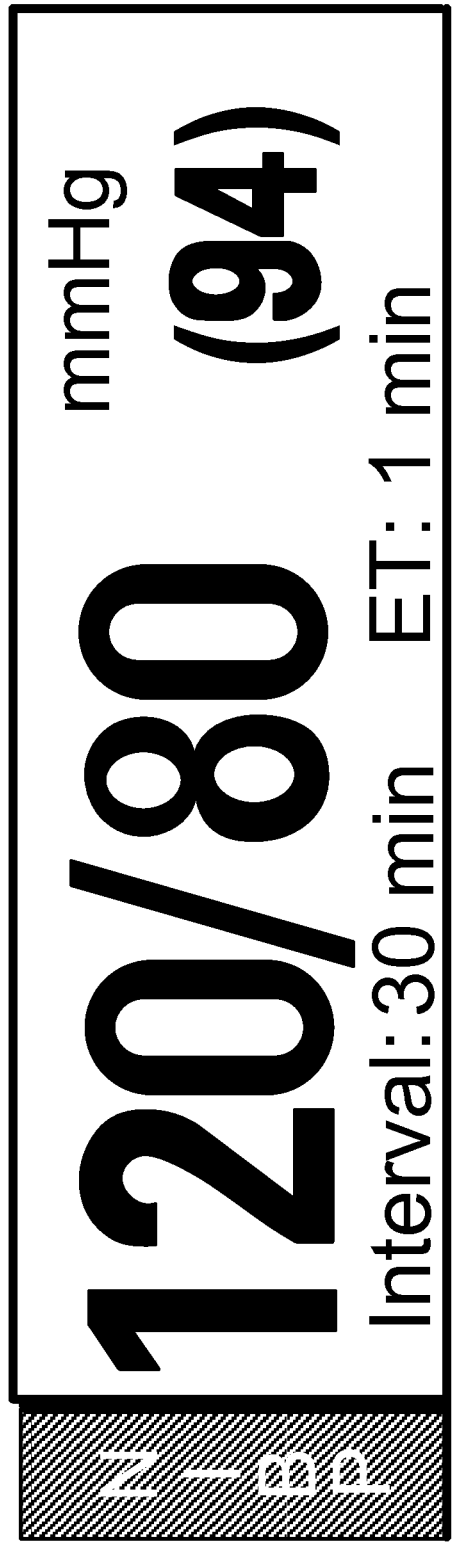
FIG. 4A is an alternative display for the encircled lower right hand corner section of the patient monitor of FIG. 1 one minute after the NIBP was measured.
Figure 4B:
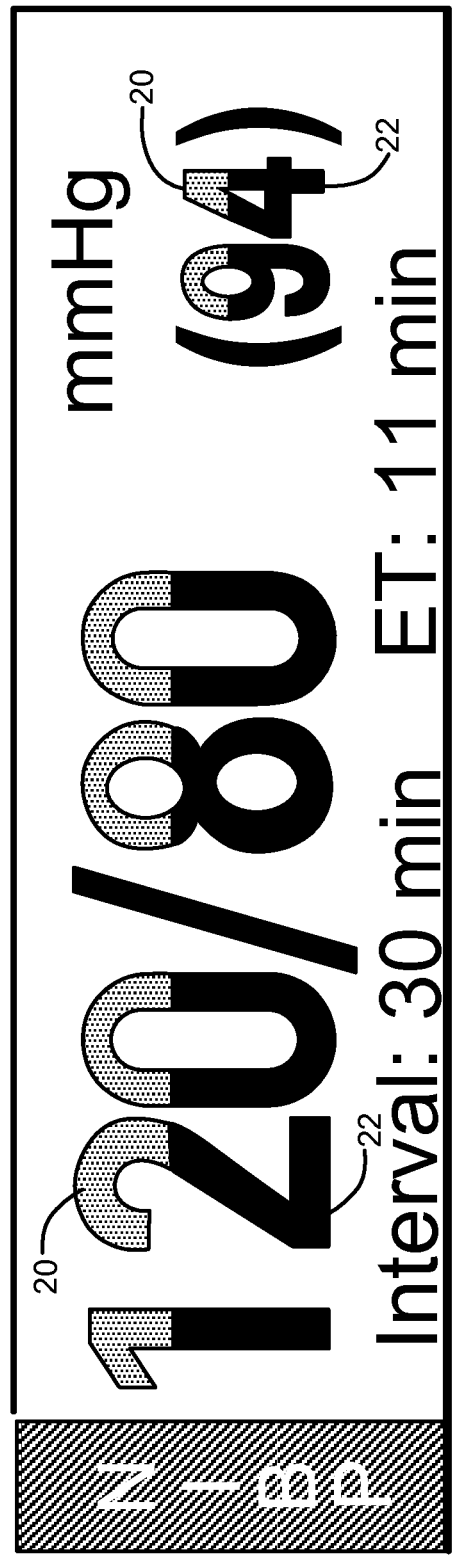
FIG. 4B is an alternative display for the encircled lower right hand corner section of the patient monitor of FIG. 1 eleven minutes after the NIBP readings were taken.
Figure 4C:
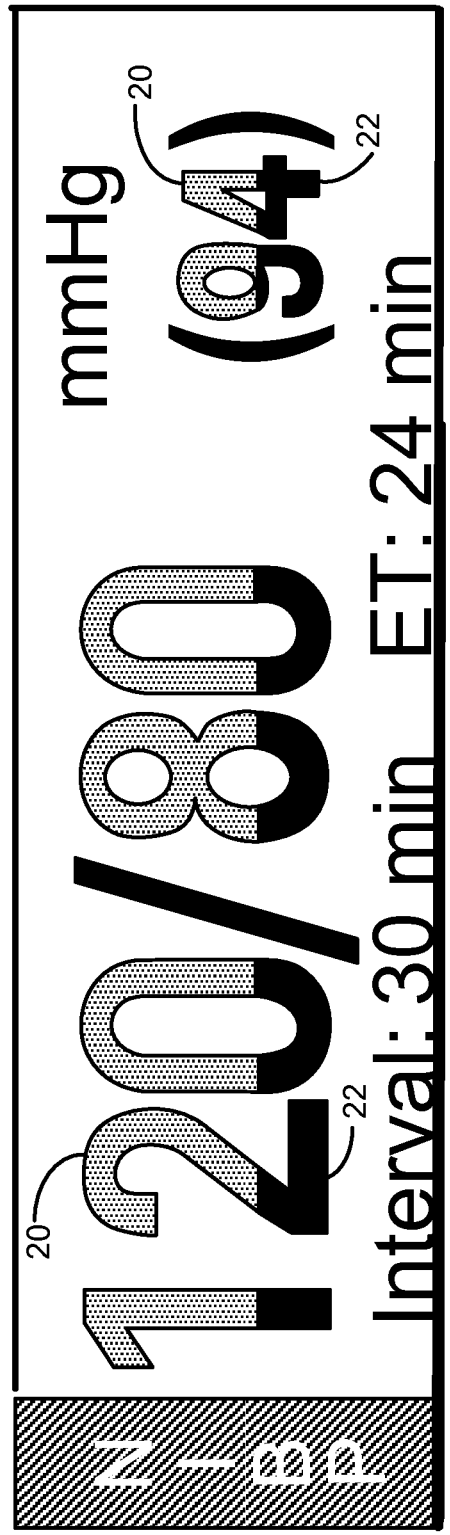
FIG. 4C is an alternative display for the encircled lower right hand corner section of the patient monitor of FIG. 1 twenty four minutes after the NIBP readings were taken.
Figure 4D:
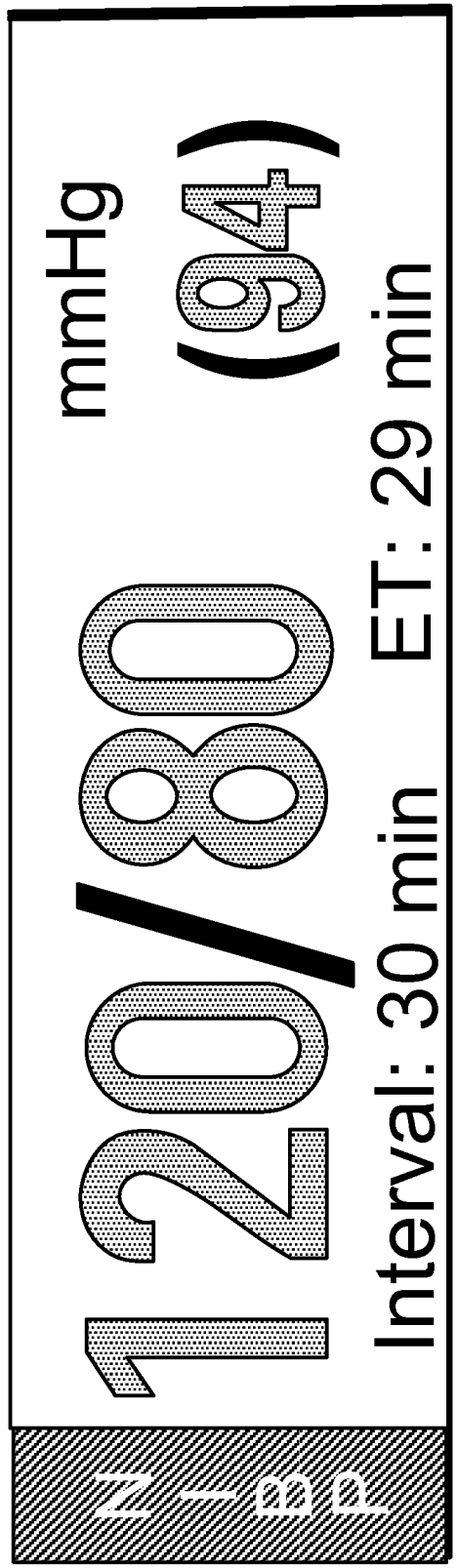
FIG. 4D is an alternative display for the encircled lower right hand corner section of the patient monitor of FIG. 1 twenty nine minutes after the NIBP readings were taken.

In FIGS. 3B-3D, a part of the upper portion 20 of the "120/80" and "94" has a white outline and a black interior while the lower portion 22 is all white. As can be seen in FIGS. 3A-3E, the upper part (black interior) 20 gets larger and the lower part (white interior) 22 gets smaller as the value becomes less reliable, which, in this example, is as time progresses. For example, the lower filled in portion 22 of FIG. 3C is smaller than the lower portion 22 in FIG. 3B. A clinician looking at the NIBP readings in FIGS. 3A-3E, for example, will thus quickly comprehend whether the displayed measurement is reliable (for example, current) or not, by looking at only a single, unitary on-screen display element. The clinician will therefore be able to mentally process both quantitative and qualitative information much more easily, quickly, and intuitively, even at a glance and in a hectic and possibly cluttered work environment. The more hollowed out the NIBP numeral the less reliable, e.g., current, the reading is. To the extent the clinician wants additional detail regarding the exact timing of the NIBP reading, he or she need only look directly below the NIBP reading, where the monitoring interval time (Interval), i.e., the amount of time between NIBP readings, and the elapsed time (ET), i.e., the amount of time passed since the displayed reading was last taken, may be displayed.

The display element can be graphically displayed and altered to reflect reliability in many different ways. As illustrated in FIGS. 4A-4D, rather than represent the upper portion 20 by an outline of the NIBP readings, a grey color, for example, may be used to represent the entire upper portion 20 of the NIBP readings. The larger the grey top section 20 of the NIBP readings grows and the smaller the black lower portion 22 shrinks, the less reliable, e.g., current, the NIBP readings are. Different colors may be used for the growing upper and shrinking lower portions 20, 22 of the NIBP readings. The use of a lighter color (or a hollowed outline of the reading) on the top portion 20 than on the bottom portion 22, however, seems to more readily communicate a decrease in reliability.

The growing and shrinking sections can also be differentiated by the use of different fills, by changing the size of the display element, etc. For example, the upper portion 20 can be filled or illustrated using cross-hatching and the lower portion 22 can be filled or illustrated using stippling, etc. Further, rather than use a top portion that grows and a bottom portion that shrinks in a downward vertical direction, vertical strips may be used that grow/shrink in a sideward direction, e.g., from left to right, so as to represent the passage of time along, e.g., the horizontal x-axis of a plot.

As can be seen in the encircled upper right hand portion of the patient monitor screen in FIG. 1, the patient's heart rate (HR) is 60 at the time the screen shot was taken. The heart rate is typically measured frequently, e.g., every time a new beat is detected, and, therefore, remains current the entire time the reading is displayed on the screen until it is replaced by a new updated reading. Therefore, there is no need to indicate to the clinician how current this reading is.

While it may not be of concern to know how current this particular physiologic parameter is, other factors may affect the reliability of the measured value. For example, the reading itself may not be very accurate due to certain conditions. Errors could be introduced, for example, due to an improperly positioned sensor or external noise or artifact pickup.

Different degrees of reliability may also be inherent in the algorithms used to calculate the physiologic parameter based on the measured patient signal. For example, some algorithms for determining such parameters as cardiac output rely on auto-regression or auto-correlation or similar techniques that have a statistical measure of accuracy or convergence, such as variance, co-variance, or standard deviation; any such factors may be converted using known methods into a measure of reliability that may be displayed using the techniques of this invention.

Various algorithms and devices are known for determining the quality of a detected physiologic signal and the accuracy of physiologic measurements estimated from these signals. For example, U.S. Pat. No. 6,675,031, discloses such an algorithm in the context of pulse oximetry and communicates the level of quality of the displayed patient physiologic parameter on a patient monitor via a warning message, such as "INVALID MEASUREMENT" or "WEAK SIGNAL," displayed adjacent the physiological patient parameter.

In another exemplary embodiment of the present invention, the processor 12 computes a patient waveform and/or physiologic parameter from a patient signal and displays such waveform and/or parameter. The processor 12 then determines the level of reliability possibly present in the displayed value of the patient parameter, e.g., using any chosen algorithm, such as the algorithm detailed in U.S. Pat. No. 6,675, 031, and communicates this information, as detailed below, via the graphic representation of the displayed patient physiologic parameter.

Figure 5A:
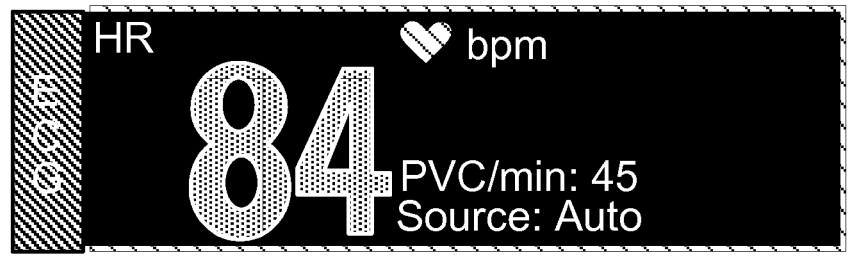
FIG. 5A is an alternative display for the encircled upper right hand corner section of the patient monitor of FIG. 1.
Figure 5B:
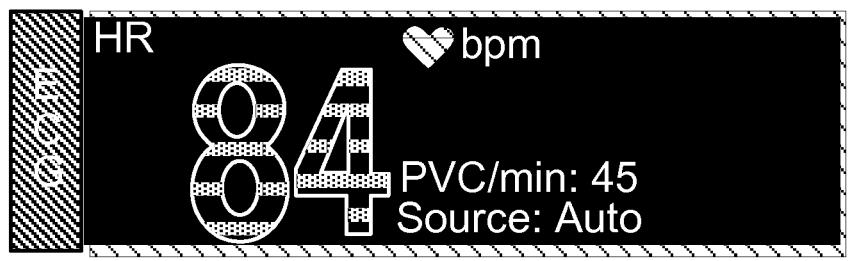
FIG. 5B is a view of an alternative display for the encircled upper right hand corner section of the patient monitor of FIG. 1.
Figure 5C:
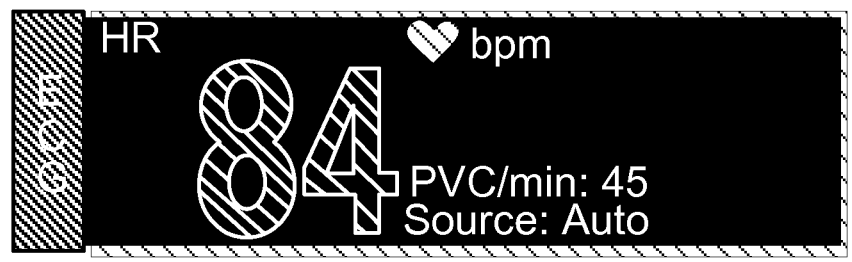
FIG. 5C is a view of an alternative display for the encircled upper right hand corner section of the patient monitor of FIG. 1.

The heart rate of 60 illustrated in FIG. 1 is depicted as a solid, completely filled numeral, which indicates that the clinician can more confidently rely on this reading as indicative of the patient's heart rate. FIGS. 5A-5C zoom in on the encircled upper right hand corner section of the monitor 10, including the heart rate information, but show the heart rate at different points in time when it is calculated to be 84. FIGS. 5A-5C show the heart rate illustrated in different manners, the manner of illustration serving as a coding for the reliability, e.g., the accuracy and validity, of the displayed heart rate reading.

In FIG. 5A, each of the numerals 8 and 4 (making up 84) is outlined white, a color lighter than the dark grey color used to fill the numerals. This depiction may be used to indicate that the reading is generally reliable but some error was introduced during the acquisition or calculation of the heart rate by the processor 12. FIG. 5B shows the numerals 8 and 4 with rather thick cross hatching. This depiction may be used to indicate more error than the depiction in FIG. 5A. Similarly, the lighter cross hatching in FIG. 5C may be used to represent even a larger degree of error.

In this manner the representation of the heart rate reading is changed not only to alert the clinician as to the possible unreliability of the heart rate reading but also as to the level of unreliability. Similar to the method detailed above to indicate how current a reading is, communicating the accuracy or validity of the displayed parameter via the graphical representation of the parameter itself minimizes the likelihood that a clinician will forget to take into consideration the reliability of the parameter before deciding on a course of treatment based on such parameter. Further, the graphical representation of the parameter makes it easier to associate the reliability information with its associated physiologic parameter and to interpret the reliability information, because a single, unitary display element gives both quantitative and qualitative information, in contrast to existing displays that require separate indicators.

In the examples of embodiments given so far, the parameter of interest, such as NIBP, will usually be represented numerically. The techniques of this invention may be used to simultaneously indicate quantity and reliability even of other types of parameters that are more suitably represented using letters, or some alphanumeric symbol or combination of alphanumeric symbols.

Moreover, the invention is not restricted to indicating only one or a few visibly discrete intermediate reliability levels between "most" and "least" reliable; rather, the display element could change more "smoothly," with any number of intermediate states (such as levels of "fill"), even up to the level of a "continuum," which would be the largest number of intermediate values possible for a given measurement precision and display and/or color palette or gray-scale resolution.

Coding methods used to communicate the accuracy or validity of a displayed parameter other than the one described above, using cross hatching and outlining of the displayed parameter, may also be used. For example, a color coding can be used in which, e.g., the displayed parameter turns more red as the parameter becomes less and less reliable. Further, the displayed parameter can be shown as an outline filled with horizontal spaced apart bars. A single top bar can be removed to indicate a small amount of error in the displayed parameter. Additional bars can be removed to indicate larger amounts of error, etc. All of these graphical methods can also be used to communicate how current the displayed parameter is. The one feature all of these coding methods have in common is that they involve the graphical representation of the displayed parameter itself, i.e., a unitary display element. The clinician need look nowhere else on the patient monitor, even to an adjacent indicator, for reliability information as it is integrated into the display of the parameter.

Although aspects of the present invention are illustrated using the NIBP and HR parameters, the present invention is in no way limited to the display of these particular parameters. The present invention is applicable to any parameter for which it is useful to communicate the reliability, including how current, or accurate, or valid the displayed reading is.

Those skilled in the art can appreciate from the foregoing description that the present invention can be implemented in a variety of forms. Therefore, while the embodiments of this invention have been described in connection with particular examples thereof, the true scope of the embodiments of the invention should not be so limited since other modifications and variations will become apparent to the skilled practitioner upon a study of the drawings and specification. Such modifications and variations are considered to be within the purview and scope of the appended claims and their equivalents.

What is claimed is:

1. A patient monitor comprising:
a display device; and
a processor configured to acquire a physiological parameter of a patient and to direct the display device to display a value of the physiological parameter,
wherein the displayed value comprises text having a circumscribing outline and a fill populating the outline, and
wherein the processor is further configured to direct the display device to smoothly shrink a level of the fill populating the outline over time to indicate a continuum of decreasing intermediate levels of reliability for the physiological parameter, such that the circumscribing outline of the displayed text value has a first level of fill at a first time and the circumscribing outline of the displayed text value has a second, lower level of fill at a second time,
wherein the levels of reliability indicate at least in part an elapsed time since the physiological parameter was acquired.

2. A method for patient monitoring comprising:
using a processor to acquire a physiological parameter of a patient;
displaying on a display device a value of the physiological parameter, wherein the displayed value comprises text having a circumscribing outline and a fill populating the outline; and
smoothly shrinking a level of the fill populating the outline over time to indicate a continuum of decreasing intermediate levels of reliability for the physiological parameter, such that the circumscribing outline of the displayed text value has a first level of fill at a first time and the circumscribing outline of the displayed text value has a second, lower level of fill at a second time,
wherein the levels of reliability indicate at least in part an elapsed time since the physiological parameter was acquired.

3. A patient monitor comprising:
a display device; and
a processor configured to acquire a physiological parameter of a patient and to direct the display device to display a value of the physiological parameter, wherein the displayed value comprises text having a fill of a first fill color, and wherein the processor is further configured to direct the display device to smoothly shrink a level of the fill over time to indicate a continuum of decreasing intermediate levels of reliability for the physiological parameter by replacing the fill with an upper fill portion having a second fill color and with a lower fill portion having the first fill color, such that a circumscribing outline of the displayed text value has a first level of fill with the first fill color at a first time and the circumscribing outline of the displayed text value has a second, lower level of fill with the first fill color at a second time, and wherein the levels of reliability indicate, at least in part, an elapsed time since the physiological parameter was acquired and wherein the reliability level is represented by the relative heights of the upper and lower portions.

4. A method for patient monitoring comprising the steps of:

using a processor to acquire a physiological parameter of a patient;

displaying on a display device a value of the physiological parameter, wherein the displayed value comprises text having a fill of a first color; and smoothly shrinking a level of the fill over time to indicate a continuum of decreasing intermediate levels of reliability for the physiological parameter, wherein the replacing comprises replacing the fill with an upper fill portion having a second fill color and with a lower fill portion having the first fill color, such that a circumscribing outline of the displayed text value has a first level of fill with the first fill color at a first time and the circumscribing outline of the displayed text value has a second, lower level of fill with the first fill color at a second time, and wherein the levels of reliability indicate, at least in part, an elapsed time since the physiological parameter was acquired and wherein the reliability level is represented by the relative heights of the upper and lower portions.

5. A patient monitor comprising:

a display device; and a processor configured to acquire a physiological parameter of a patient and to direct the display device to display a value of the physiological parameter, wherein the displayed value comprises text having a circumscribing outline and a fill populating the outline, and wherein the processor is further configured to direct the display to smoothly shrink a level of the fill populating the outline over time to indicate a continuum of decreasing intermediate levels of reliability for the physiological parameter, such that the circumscribing outline of the displayed text value has a first level of fill at a first time and the circumscribing outline of the displayed text value has a second, lower level of fill at a second time, and wherein the levels of reliability being based, at least in part, on a statistical measure of accuracy of an algorithm used by the processor to determine the value of the physiological parameter.

6. The patient monitor of claim 5, wherein the processor is configured to direct the display device to remove fill from an upper portion of the fill populating the circumscribing outline with a lower portion remaining, and wherein the level of reliability is represented by the relative heights of the upper and lower portions.

7. A method for patient monitoring comprising:

using a processor to acquire a physiological parameter of a patient;

displaying on a display device a value of the physiological parameter, wherein the displayed value comprises text having a circumscribing outline and a fill populating the outline; and smoothly shrinking a level of the fill populating the outline over time to indicate a continuum of decreasing intermediate levels of reliability for the physiological parameter, such that the circumscribing outline of the displayed text value has a first level of fill at a first time and the circumscribing outline of the displayed text value has a second, lower level of fill at a second time, and wherein the levels of reliability being based, at least in part, on a statistical measure of accuracy of an algorithm used by the processor to determine the value of the physiological parameter.

8. The method of claim 7, wherein smoothly shrinking a level of the fill populating the outline comprises removing fill from an upper portion of the fill populating the outline with a lower portion remaining, and wherein the level of reliability is represented by the relative heights of the upper and lower portions.

9. The patient monitor of claim 1, wherein the processor is configured to direct the display device to remove fill from an upper portion of the fill populating the outline with a lower portion remaining, and wherein the level of reliability is represented by the relative heights of the upper portion and the lower portion.

10. The patient monitor of claim 1, wherein the processor is configured to direct the display device to remove fill from a left portion of the fill populating the outline with a right portion remaining, and wherein the level of reliability is represented by the relative sizes of the left portion and the right portion.

11. The method of claim 2, wherein smoothly shrinking a level of the fill populating the outline comprises removing fill from an upper portion of the fill populating the outline with a lower portion remaining, and wherein the level of reliability is represented by the relative heights of the upper portion and the lower portion.

12. The method of claim 2, wherein smoothly shrinking a level of the fill populating the outline comprises removing fill from a left portion of the fill populating the outline with a right portion remaining, and wherein the reliability level is represented by the relative sizes of the left portion and the right portion.

13. The method of claim 2, wherein smoothly shrinking a level of the fill populating the outline begins after the physiological parameter is acquired.

14. The patient monitor of claim 5, wherein the processor is configured to direct the display device to remove fill from a left portion of the fill populating the outline with a right portion remaining, and wherein the level of reliability is represented by the relative sizes of the left portion and the right portion.

15. The method of claim 7, wherein smoothly shrinking a level of the fill populating the outline comprises removing fill from a left portion of the fill populating the outline with a right portion remaining, and wherein the reliability level is represented by the relative sizes of the left portion and the right portion.

* * * * *